US 6,544,930 B2

(12) United States Patent
Wright

(10) Patent No.: US 6,544,930 B2
(45) Date of Patent: Apr. 8, 2003

(54) COMPACT STORAGE AND SHIPPING SYSTEM FOR GLYPHOSATE HERBICIDE

(75) Inventor: Daniel R. Wright, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/992,728

(22) Filed: Nov. 16, 2001

(65) Prior Publication Data

US 2002/0065199 A1 May 30, 2002

Related U.S. Application Data

(63) Continuation of application No. 09/444,766, filed on Nov. 22, 1999, now Pat. No. 6,277,788.
(60) Provisional application No. 60/109,514, filed on Nov. 23, 1998.

(51) Int. Cl.[7] ............................................. A01N 57/02
(52) U.S. Cl. ....................................................... 504/206
(58) Field of Search ................................. 504/206

(56) References Cited

U.S. PATENT DOCUMENTS

| | | |
|---|---|---|
| 3,799,758 A * | 3/1974 | Franz .......................... 71/86 |
| 3,853,530 A | 12/1974 | Franz |
| 3,977,860 A | 8/1976 | Franz |
| 4,140,513 A | 2/1979 | Prill |
| 4,315,765 A | 2/1982 | Large |
| 4,405,531 A | 9/1983 | Franz |
| 4,481,026 A | 11/1984 | Prisbylla |
| 4,507,250 A | 3/1985 | Bakel |
| 5,652,197 A | 7/1997 | Claude et al. |
| 5,668,085 A | 9/1997 | Forbes et al. |
| 5,750,468 A | 5/1998 | Wright et al. |

FOREIGN PATENT DOCUMENTS

| | | |
|---|---|---|
| GB | 1 588 079 | 4/1981 |
| WO | WO 98/33384 | 8/1998 |
| WO | WO 98/33385 | 8/1998 |
| WO | WO 00/15037 | 3/2000 |

OTHER PUBLICATIONS

Ross et al. Applied Weed Science. Burgess Pub. Co. p. 113–128. 1985.*

* cited by examiner

Primary Examiner—S. Mark Clardy
(74) Attorney, Agent, or Firm—Senniger, Powers, Leavitt & Roedel; Joseph A. Schaper

(57) ABSTRACT

A storage and shipping system for glyphosate herbicide is provided, comprising a container having a capacity of about 0.1 to about 100,000 liters or more, substantially filled with an aqueous solution of glyphosate, predominantly in the form of one or a mixture of the potassium and monoethanolammonium salts thereof, the solution having a glyphosate acid equivalent concentration of at least about 30 percent by weight. The storage and shipping system, by virtue of the relatively high specific gravity of the glyphosate salt solution, holds a greater weight of glyphosate than a system comprising an identical container substantially filled with an aqueous solution of the isopropylammonium salt of glyphosate at the same glyphosate concentration by weight. Alternatively, the container of the storage and shipping system can be smaller than that of a container holding the same weight of glyphosate in the form of the isopropylammonium salt. Further, a larger number of such smaller containers can be shipped in a given enclosed volume, thereby enabling the shipment of a larger weight of glyphosate in a single consignment.

18 Claims, 4 Drawing Sheets

COMPACT STORAGE AND SHIPPING SYSTEM FOR GLYPHOSATE HERBICIDE

This application is a continuation application of U.S. Ser. No. 09/444,766, filed Nov. 22, 1999, now U.S. Pat. No. 6,277,788 which claims the benefit of U.S. Provisional Application No. 60/109,514, filed Nov. 23, 1998 the disclosures of which are expressly incorporated herein by reference.

FIELD OF THE INVENTION

The present invention relates to a system for storage and transportation of an agricultural chemical. More particularly, it relates to an article of manufacture useful in warehousing and shipping of the herbicide glyphosate.

BACKGROUND OF THE INVENTION

The agricultural industry presents numerous logistical problems to the supplier of goods consumed in that industry, these problems being unique to agriculture or at least more acute than in most other industries. Individual production units in the agricultural industry (such units are called "farms" herein regardless of whether they fit the traditional image of farms) are more numerous and more geographically dispersed than in any other industry and, even in highly developed countries such as those of North America and Western Europe, are often relatively remote from major transport arteries. For these reasons, transportation costs, both inward and outward, are a significant burden on the industry and improvements in efficiency of transportation are continually sought in order to reduce these costs.

Distribution channels for goods required by the agricultural industry have evolved to deal with the geographical dispersion and large number of farms. In some cases, goods are shipped directly from the point of production to individual farms, but this is rare and is economically feasible only for the largest farms. Generally there is at least one, often more than one, step in the distribution channel between the original supplier and the farm gate. For example, the manufacturer of a good destined for use on a farm supplies a wholesale distribution company, which supplies a retailer or farm cooperative, which in turn supplies the individual farm. Distributors, retailers and cooperatives therefore maintain inventories of such goods, incurring warehousing costs that add to the cost ultimately borne by the farm operation. Improvements in efficiency of storage are therefore also sought, again in order to reduce costs.

Where the good in question is a pesticide, for example a herbicide, the benefits obtainable from improved efficiency of transportation and storage are particularly great. Pesticide products must generally be transported and stored in containers that are more expensive per unit of capacity than those used for many other products such as seeds and fertilizers. Expensive containers are used because of the great importance of container integrity arising from the high price/volume ratio of most pesticides and the fact that many pesticides are potentially hazardous if spilled or leaked.

Typically, therefore, pesticides are stored and transported in as concentrated or compact a form as possible without sacrificing ease of handling by the end-user, who has in most cases to dilute the pesticides in water or another carrier before applying the pesticides to crops, weeds or soil. The larger the amount of pesticidal active ingredient that can be accommodated in a container of given capacity, the lower are the costs of transportation and storage per unit of active ingredient and per unit area of land ultimately to be treated with that active ingredient. That the present state of the art sets an upper limit on the efficiency of packing of pesticides in containers for storage and shipping is well illustrated in the case of the herbicide glyphosate (N-phosphonomethylglycine).

Glyphosate is "the largest selling agrochemical in the global market" with an estimated annual production of 93,420–114,180 tonnes (Wood Mackenzie Agrochemical Service, Agrochemicals Product Database, 1998). It finds uses for control of unwanted vegetation in virtually every agricultural production system, as well as in forestry, industrial, municipal, residential, rights-of-way, amenity and other applications. Glyphosate is an acid that is relatively insoluble in water (1.16% by weight at 25° C.). For this reason it is typically formulated as a water-soluble salt in aqueous solution.

Monobasic, dibasic and tribasic salts of glyphosate can be made. However, it is generally preferred to formulate glyphosate and apply glyphosate to plants in the form of a monobasic salt. The most widely used salt of glyphosate is the mono(isopropylammonium), often abbreviated to IPA, salt. Commercial herbicides of Monsanto Company having the IPA salt of glyphosate as active ingredient include Roundup®, Roundup® Ultra, Roundup® Xtra and Rodeo® herbicides. All such commercial products take the form of concentrated aqueous solutions of glyphosate IPA salt, in most cases together with inert formulation ingredients, principally surfactants. Other glyphosate salts which have been commercially formulated as concentrated aqueous solutions include the mono(trimethylsulfonium), often abbreviated to TMS, salt, used for example in Touchdown® herbicide of Zeneca.

The great diversity of global markets for glyphosate herbicides has led to a corresponding diversity of container types and sizes, and to a number of more complex storage and shipping systems, for concentrated liquid aqueous formulations of glyphosate salts. Containers used for storing and shipping such formulations are typically constructed of a durable plastic such as high density polyethylene (HDPE), although large bulk tanks are often constructed of other materials such as stainless steel.

Small containers, ranging in capacity from about 0.1 liter to about 10 liters, including the standard 2.5 gallon (9.46 liter) containers widely used in the United States, typically take the form of jugs or flasks with a replaceable screw-cap. They are generally designed for single use and are typically not returned to the supplier when empty, instead being disposed of by the end-user in accordance with local agricultural chemical container disposal guidelines, procedures, regulations or laws. Commonly, a plurality of these small containers are packaged within a single box and a plurality of such boxes are shipped on a pallet. During shipment, the small containers (usually within boxes on pallets) can be disposed in an enclosed volume such as provided by a rail boxcar or road truck, the hold of a ship or aircraft, or a modular box container adapted for transport by road, rail and water.

Larger single-use containers, ranging in capacity up to about 200 liters, for example about 50 to about 200 liters, are commonly in the form of drums, and can be shipped in an enclosed volume as described above, one or more per pallet or unpalleted.

Increasing volumes of liquid aqueous glyphosate products are being purchased by end-users in a large refillable container sometimes known as a shuttle, which typically has an integral pump or connector for an external pump to permit transfer of liquid. Shuttles have a capacity of about 200 to about 2000 liters and are commonly shipped on a pallet.

Liquid aqueous glyphosate products are also shipped in bulk, in large tanks having a capacity of up to about 100,000 liters. The liquid is commonly transferred by pumping to a storage tank at a facility operated by a wholesaler, retailer or cooperative, from which it can be further transferred to shuttles or smaller containers for onward distribution. Bulk shipment is also used for concentrated glyphosate salt solutions to be used as a raw material for preparation of formulated herbicidal products contining additional ingredients such as a surfactant.

A modular bulk shipping tank adapted for road, rail and water transportation typically has a capacity of about 15,000 to about 20,000 liters. A tank truck for road transportation typically has a capacity of about 20,000 to about 25,000 liters. A railcar tank typically has a capacity of about 75,000 to about 90,000 liters.

It will be clear from the storage and shipping containers illustratively described above that all have a limited capacity. Furthermore, when containers are shipped or stored in an enclosed volume, that enclosed volume also has a limited capacity.

Storage and shipping costs for most modes of transportation are primarily related to volume, therefore a system that would permit more compact packing of glyphosate into the available volume or capacity would significantly reduce such costs per unit of glyphosate stored or shipped. Other advantages of such a system would include the convenience and cost saving to the end-user of having fewer containers for disposal, and the resulting environmental benefits; reduced frequency of refilling of shuttles or storage tanks; and further advantages that will be apparent from the disclosure herein.

Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

The highest concentration at which glyphosate IPA salt can conveniently be stored and transported as an aqueous solution is about 62% by weight. Its limit of solubility is only slightly higher than this. As it is the glyphosate rather than the IPA component that is active as a herbicide, concentrations are most usefully expressed in terms of glyphosate acid equivalent (a.e.). A 62% by weight glyphosate IPA salt solution contains about 46% glyphosate a.e. by weight. Even at this concentration, problems can occur, including crystallization of glyphosate salt when stored for prolonged periods of time at low temperatures, and difficulties in pouring and/or pumping as a result of the high viscosity of the solution, especially at low temperatures.

Few salts of glyphosate are soluble enough in water to permit convenient storage and shipping at concentrations significantly higher than 62% by weight. The TMS salt is highly soluble and is useful in some situations, but cannot substitute for the IPA salt in all applications.

It might be thought that by selecting a counterion for glyphosate, such as ammonium ion, having significantly lower molecular weight than IPA, higher glyphosate a.e. concentrations would be possible. For example, at a salt concentration of 36% by weight, a glyphosate ammonium salt solution contains about 33% a.e. by weight, whereas a glyphosate IPA salt solution contains only about 27% a.e. by weight. Unfortunately, the solubility of glyphosate ammonium salt in water is much lower than that of the IPA salt, thus this apparent advantage cannot be exploited in highly concentrated solutions, for example of 40% a.e. by weight or higher.

An approach that has found utility has been to prepare the glyphosate as a dry salt. Many glyphosate salts, including the IPA and TMS salts, are difficult and expensive to prepare in a dry form, but the ammonium and sodium salts are more amenable to this approach. For example, a dry water-soluble powder or granular formulation of glyphosate ammonium salt containing about 95% by weight of that salt can be manufactured on a commercial scale; such a formulation has a glyphosate a.e. content of about 86% by weight. This would appear at first sight to provide an excellent solution to the problem of packing more glyphosate a.e. into a container of given capacity. Unfortunately, however, the bulk density of such a powder or granular formulation is rather low, so that the benefit is not as great as might be thought. Also, many end-users and many distributors prefer a liquid product because of flexibility in handling, thus the need remains for a more compact storage and shipping system for a glyphosate salt in liquid form.

Among the water-soluble salts of glyphosate known in the literature, but never used commercially, are the potassium salt and the monoethanolammonium (MEA) salt. These salts are disclosed, for example, by Franz in U.S. Pat. No. 4,405,531 cited above, among a very long list of salts of glyphosate useful as herbicides.

Few herbicides have been commercialized as their potassium or MEA salts. The Pesticide Manual, 11th Edition, 1997 lists as potassium salts the auxin type herbicides 2,4-DB ((2,4-dichlorophenoxy)butanoic acid), dicamba (3,6-dichloro-2-methoxybenzoic acid), dichlorprop (2-(2,4-dichlorophenoxy)propanoic acid) and MCPA ((4-chloro-2-methylphenoxy)acetic acid), and picloram (4-amino-3,5,6-trichloro-2-pyridinecarboxylic acid), the active ingredient of certain herbicide products sold by DowElanco under the trademark Tordon®. Clopyralid (3,6-dichloro-2-pyridinecarboxylic acid) is formulated as its MEA salt in certain herbicide products sold by DowElanco under the trademark Lontrel®.

Glyphosate potassium salt has a molecular weight of 208. Glyphosate MEA salt has a molecular weight of 230, very similar to that of glyphosate IPA salt (228).

Solubility in water of the potassium and MEA salts of glyphosate is believed not to be recorded in prior art but is readily determined by procedures familiar to those skilled in the art. Similarly, aqueous solutions of these salts at concentrations greater than about 40% by weight are believed not to have been specifically disclosed, thus any unusual or unpredicted properties of such solutions have not been publicly known. Concentrations expressed as percent by weight herein relate to parts by weight of salt or acid equivalent per 100 parts by weight of solution.

It can now be disclosed that glyphosate potassium salt has been determined to have a solubility in pure water at 20° C. of about 54% by weight, that is, about 44% glyphosate acid equivalent (a.e.) by weight. It can further be disclosed that glyphosate MEA salt has been determined to have a solubility in pure water at 20° C. of about 64% by weight of solution, that is, about 47% glyphosate a.e. by weight. The solubility of the MEA salt is very similar to the solubility of the IPA salt. Thus a simple aqueous solution concentrate of glyphosate MEA salt can readily be provided at a concentration of, for example, 46% a.e. by weight, comparable to that commercially obtainable with glyphosate IPA salt, as in the aqueous solution concentrate available from Monsanto Company under the name MON 0139.

While it would be desirable, as indicated above, to have a compact storage and shipping system for glyphosate salt, it would also be desirable to have a compact storage and shipping system for glyphosate salt accompanied by one or more surfactants in an agronomically useful amount.

An "agronomically useful amount" means a sufficient amount of the surfactant or surfactants to provide a benefit in terms of improved herbicidal effectiveness by comparison with the glyphosate salt applied in the absence of surfactant. It would be especially desirable to have a compact storage and shipping system for glyphosate salt accompanied by one or more surfactants in an amount sufficient to provide herbicidal effectiveness on one or more important weed species at least equal to that of current commercial glyphosate IPA salt products such as Roundup® herbicide, without the need for further surfactant to be added by the user.

The glyphosate composition forming part of a compact storage and shipping system must be storage-stable. By "storage-stable", in the context of a concentrated aqueous solution of glyphosate salt, is meant not forming crystals of glyphosate or salt thereof on exposure to a temperature not lower than about 0° C. for a period of up to about 7 days. Ideally the composition should withstand temperatures not lower than about −10° C. for up to about 7 days without crystal formation, even in the presence of seed crystals of the glyphosate salt. Where the glyphosate composition also contains a surfactant, storage-stability requires, at a minimum, that the composition does not exhibit phase separation at temperatures of about 50° C. or lower, ideally at temperatures of about 60° C. or lower. Preferably such a surfactant-containing composition should also withstand temperatures not lower than about 0° C. for up to about 7 days without crystal formation.

A surfactant that is described herein as "compatible" with a glyphosate salt at specified surfactant and glyphosate a.e. concentrations is one that provides a storage-stable composition as defined immediately above containing that surfactant and salt at the specified concentrations.

Users of liquid herbicidal products typically meter the dosage by volume rather than by weight, and such products are usually labeled with directions for suitable use rates expressed in volume per unit area, e.g., liters per hectare (l/ha) or fluid ounces per acre (oz/acre). Thus the concentration of herbicidal active ingredient that matters to the user is not percent by weight, but weight per unit volume, e.g., grams per liter (g/l) or pounds per gallon (lb/gal). In the case of glyphosate salts, concentration is often expressed as grams of acid equivalent per liter (g a.e./l).

Historically, surfactant-containing glyphosate IPA salt products such as Roundup® and Roundup® Ultra herbicides of Monsanto Company have most commonly been formulated at a glyphosate concentration of about 360 g a.e./l. The surfactant-containing glyphosate TMS salt product Touchdown® of Zeneca has been formulated at a glyphosate concentration of about 330 g a.e./l. Products at lower a.e. concentration, i.e., more dilute, are also sold in some markets, but carry a cost penalty per unit of glyphosate they contain, primarily reflecting packaging, shipping and warehousing costs.

Further benefits in cost saving and in convenience to the user are possible if the concentrated aqueous solution of glyphosate salt forming part of a compact storage and shipping system and having an agronomically useful amount of surfactant can be provided at a glyphosate concentration significantly higher than 360 g a.e./l, for example about 420 g a.e./l or higher, or even about 480 g a.e./l or higher. It would be especially beneficial if such a compact storage and shipping system could further permit easy pouring and/or pumping of the concentrated solution, even at low temperatures.

SUMMARY OF THE INVENTION

The present invention takes advantage of a previously unknown and surprising property of concentrated aqueous solutions of the potassium and MEA salts of glyphosate, namely that such solutions have a very high specific gravity by comparison with aqueous solutions of most other agronomically useful salts of glyphosate, including the IPA salt, at the same glyphosate a.e. concentration. Accordingly, at a given percent concentration by weight, an aqueous solution of glyphosate potassium or MEA salt contains a higher weight of active ingredient per unit volume of the composition than a corresponding composition of glyphosate IPA salt. This finding is illustrated for the MEA salt in FIG. 1.

In one embodiment of the invention, therefore, there is provided a storage and shipping system for glyphosate herbicide comprising a container having a capacity of about 0.1 to about 100,000 liters or more, substantially filled with an aqueous solution of glyphosate, predominantly in the form of one or a mixture of the potassium and monoethanolammonium salts thereof, the solution having a glyphosate acid equivalent concentration between about 30 percent by weight and a maximum percent by weight dictated by the solubility of the glyphosate salt or mixture of salts present. Preferably the glyphosate is predominantly in the form of the monoethanolammonium salt thereof and the solution has a glyphosate acid equivalent concentration of about 30 to about 48 percent by weight, more preferably about 40 to about 48 percent by weight.

Figure 2:
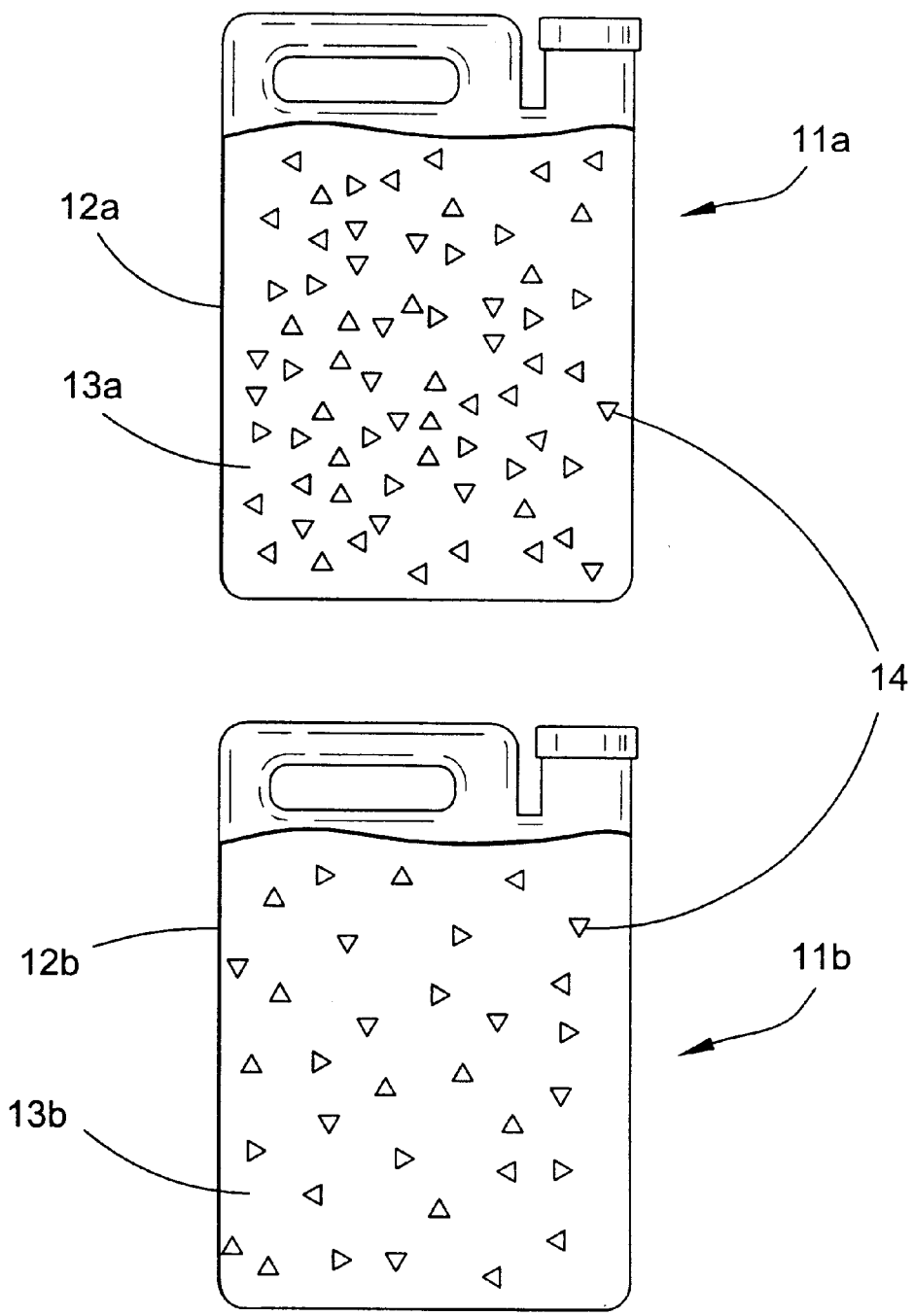
FIG. 2 is a diagram of a storage and shipping system for glyphosate herbicide comprising a container of fixed capacity, illustratively a 10 liter jug, in accordance with the present invention, by comparison with a prior art system comprising an identical container, wherein the system of the invention permits storage and shipping of a larger weight of glyphosate than the prior art system.

As illustrated in FIG. 2, such a storage and shipping system, by virtue of the relatively high specific gravity of the glyphosate salt solution, holds a greater weight of glyphosate acid equivalent than a system comprising an identical container substantially filled with an aqueous solution of the isopropylammonium salt of glyphosate at the same glyphosate acid equivalent concentration by weight.

Figure 3:
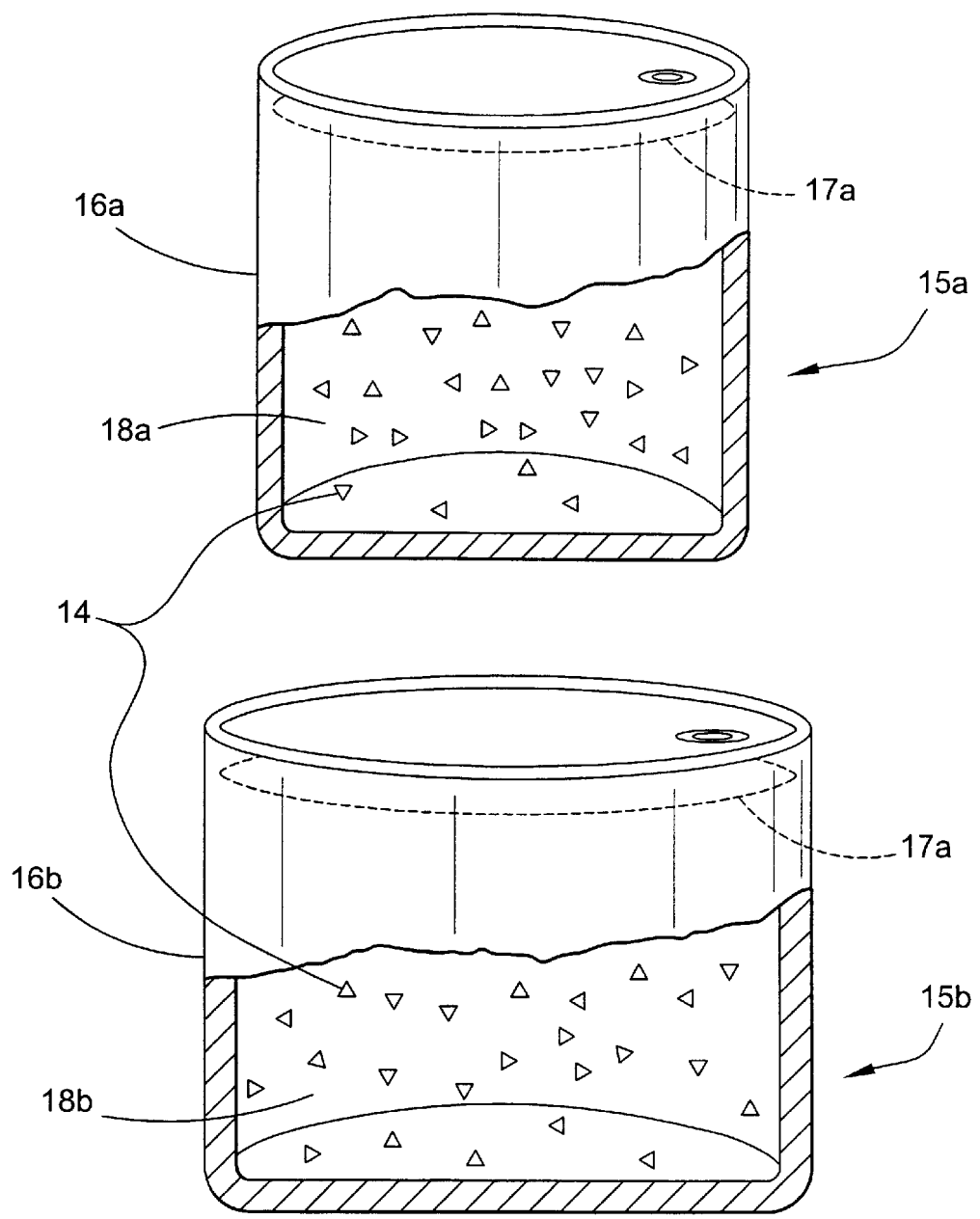
FIG. 3 is a cutaway diagram of a storage and shipping system for glyphosate herbicide comprising a container of fixed capacity, illustratively a drum, in accordance with the present invention, by comparison with a prior art system, wherein the system of the invention has a smaller container than that of the prior art system yet permits storage and shipping of the same weight of glyphosate. The diagram is not to scale; the difference in container size is exaggerated for clarity.
Figure 4:
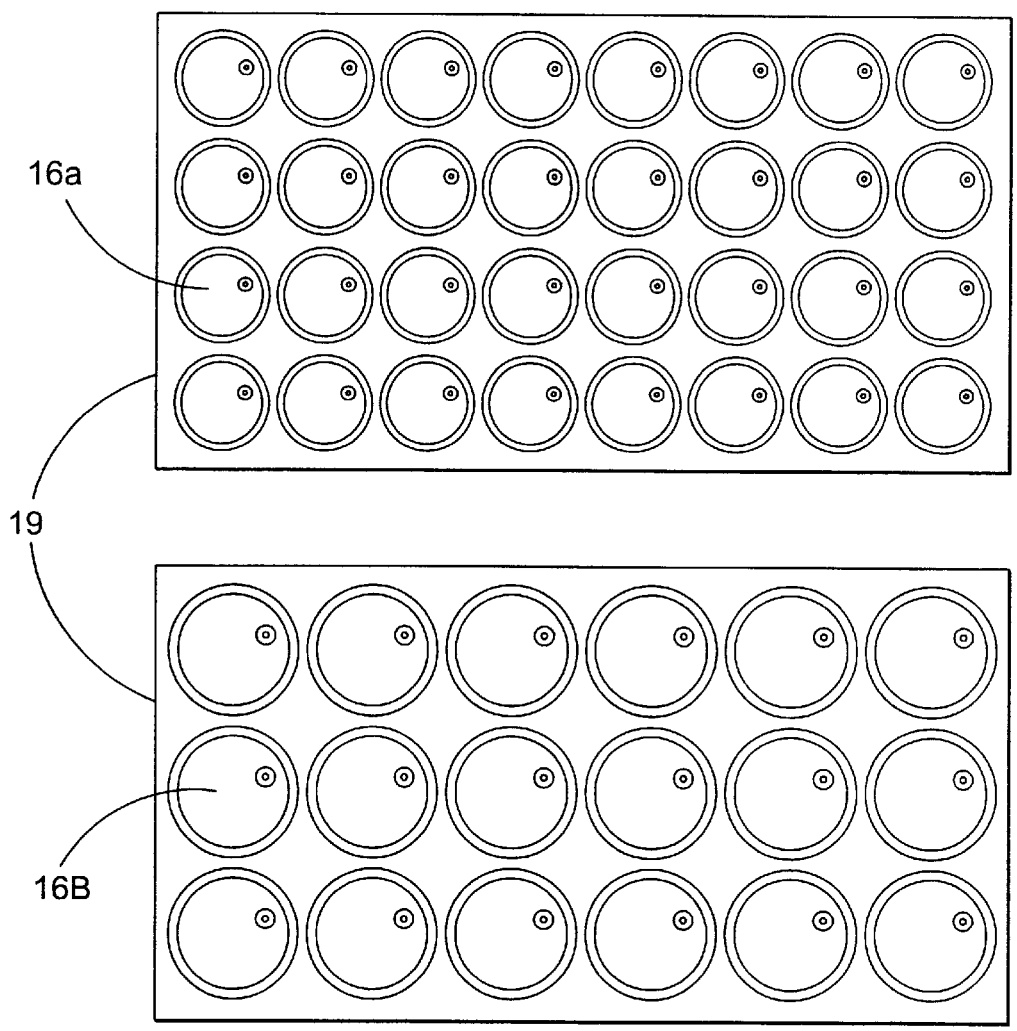
FIG. 4 is a diagram of an enclosed shipping volume, in plan view, wherein are disposed a multiplicity of containers pertaining to a storage and shipping system of the invention as shown in FIG. 3. The diagram is not to scale; the difference in container size is exaggerated for clarity.

Alternatively, as illustrated in FIG. 3, the container of such a storage and shipping system can be smaller than that of a container holding the same weight of glyphosate acid equivalent in the form of the isopropylammonium salt. Further, as illustrated in FIG. 4, a larger number of such smaller containers can be shipped in a given enclosed volume, thereby enabling the shipment of a larger weight of glyphosate acid equivalent in a single consignment.

In a related embodiment of the invention, there is provided a storage and shipping system for glyphosate herbicide comprising a container having a capacity of about 0.1 to about 100,000 liters or more, partially or completely filled with an aqueous solution of glyphosate, predominantly in the form of one or a mixture of the potassium and monoethanolammonium salts thereof, the solution having a glyphosate acid equivalent concentration between about 360 grams per liter of the solution and a maximum concentration dictated by the solubility of the glyphosate salt or mixture of glyphosate salts present. Preferably the container is substantially filled with the solution. Preferably the glyphosate is predominantly in the form of the monoethanolammonium salt thereof and the solution has a glyphosate acid equivalent concentration of about 360 to about 600 grams per liter of the solution.

Such a storage and shipping system facilitates transfer of the solution into or out of the container by pouring or pumping, as a result of the solution having a significantly lower viscosity than a corresponding solution of the isopropylammonium salt of glyphosate at the same acid equivalent weight/volume concentration.

The term "substantially filled" herein means that the volume of the glyphosate salt solution in the container is not substantially less than the design capacity or nominal capacity of the container, for example not less than about 95% of that design capacity or nominal capacity. Thus, illustratively, a container of commerce sold or labeled as a "10 liter jug" is considered to be "substantially filled" if it contains 9.5–10 liters of glyphosate salt solution, even if, when it contains 10 liters, there remains an air space at the head of the container after filling.

In a further embodiment of the invention, it has been found that in a concentrated aqueous solution, an unexpectedly high weight/volume concentration of glyphosate MEA salt can be obtained in the presence of an agronomically useful amount of surfactant. The choice of surfactant has been found to be important to achieving this result.

In such embodiment, therefore, the present invention provides a storage and shipping system for glyphosate herbicide comprising a container having a capacity of about 0.1 to about 100,000 liters or more, partially or completely filled with a composition that comprises:

(1) water;
(2) glyphosate, predominantly in the form of the monoethanolammonium salt thereof, in solution in the water in an amount of about 360 to about 570 grams glyphosate acid equivalent per liter of the composition; and
(3) a surfactant component in solution or stable dispersion in the water, comprising one or more surfactants in a total amount of about 20 to about 200 grams per liter of the composition, this surfactant component being selected such that the composition exhibits no phase separation at temperatures of about 50° C. or lower and preferably exhibits substantially no crystallization of glyphosate or salt thereof when stored at a temperature not lower than about 0° C. for a period of up to about 7 days.

Although at present the maximum capacity for a container used for storage and/or shipping of glyphosate herbicide is about 100,000 liters, it will readily be understood that the invention is not limited by such current practice. For example, if it should be contemplated to transport glyphosate herbicide in a tanker ship or barge having one or more tanks significantly greater in capacity than 100,000 liters, the benefits of using glyphosate potassium or MEA salt set out herein will be just as evident as in containers of lesser volume.

Preferably the container, regardless of its capacity, is substantially filled with the composition.

The word "predominantly" in the context of glyphosate salts means that at least about 50%, preferably at least about 75% and more preferably at least about 90%, by weight of the glyphosate, expressed as a.e., is present as the indicated salt or mixture of salts. The balance can be made up of other salts and/or glyphosate acid so long as the indicated properties of the composition remain within the limits stated.

DETAILED DESCRIPTION OF THE INVENTION

As indicated above, concentrated aqueous solutions of glyphosate potassium and MEA salts have surprisingly been found to have exceptionally high specific gravity. Table 1 shows, by way of example, specific gravities measured for 30% glyphosate a.e. by weight solutions of the potassium and MEA salts of glyphosate by comparison with other organic ammonium and other salts of current or previous commercial interest. Specific gravities are measured using a Mettler DA-300 Density/Specific Gravity Meter.

TABLE 1

Specific gravity (20/18.6° C.) of 30% a.e. by weight glyphosate monobasic salt solutions.

| Salt | Specific Gravity |
| --- | --- |
| potassium | 1.2539 |
| monoethanolammonium (MEA) | 1.2357 |
| isopropylammonium (IPA) | 1.1554 |
| n-propylammonium | 1.1429 |
| methylammonium | 1.1667 |
| ethylammonium | 1.1599 |
| ammonium | 1.1814 |
| trimethylsulfonium (TMS) | 1.1904 |

Thus 1 liter of 30% a.e. by weight glyphosate potassium salt solution at 20° C. contains approximately 376 g glyphosate a.e./l, whereas 1 liter of 30% a.e. by weight glyphosate IPA salt solution at 20° C. contains approximately 347 g glyphosate a.e./l. In other words, at equal a.e. weight concentration, the potassium salt solution delivers about 8% more glyphosate a.e. per liter.

Similarly, 1 liter of 30% a.e. by weight glyphosate MEA salt solution at 20° C. contains approximately 371 g glyphosate a.e./l. Therefore at equal a.e. weight concentration, the MEA salt solution delivers about 7% more glyphosate a.e. per liter than an IPA salt solution.

Whether the potassium or MEA salt is employed, the minimum useful concentration in the aqueous solution is about 30% a.e. by weight and is preferably about 40% a.e. by weight. The maximum concentration, dictated by the limit of solubility at 20° C., is about 44% a.e. by weight in the case of the potassium salt and about 47% a.e. by weight in the case of the MEA salt.

A storage and shipping system employing glyphosate potassium salt solution is of particular utility where the solution does not additionally contain surfactant and/or where the solution is not destined for use in preparing concentrated surfactant-containing formulations. Only a few surfactant types have been found to be compatible in agronomically useful amounts with high concentrations of glyphosate potassium salt.

However, a storage and shipping system for glyphosate herbicide employing the MEA salt has great utility for both surfactantless and surfactant-containing solutions. In a surfactant-containing solution, the maximum glyphosate concentration is constrained not only by the limit of solubility of the MEA salt in water but also by the limits of surfactant compatibility. In such solutions, the advantages of the MEA salt can mean that (a) a higher maximum glyphosate a.e. weight/volume concentration is achieved than with the IPA salt in the presence of the same compatible surfactant at the same surfactant concentration, (b) a higher compatible surfactant concentration is achieved than with the IPA salt at the same glyphosate a.e. weight/volume concentration, (c) at given weight/volume concentrations of glyphosate a.e. and surfactant, improved storage-stability is achieved over a corresponding composition prepared with the IPA salt, and/or (d) at given weight/volume concentrations of glyphosate a.e. and surfactant, improved pouring and pumping properties are achieved over a corresponding composition prepared with the IPA salt as a result of lower viscosity.

The advantages of storage and shipping systems of the present invention become less as glyphosate concentration in the aqueous solution is reduced and are only marginal at a glyphosate concentration lower than about 360 g a.e./l, i.e., lower than the concentration found in such commercial glyphosate IPA salt products as Roundup® herbicide. In preferred systems of the invention, glyphosate concentration in the aqueous solution is not lower than 420 g a.e./l or about 420 g a.e./l, in particularly preferred systems not lower than about 480 g a.e./l, for example about 480 to about 540 g a.e./l. It is believed that the practical upper limit of glyphosate concentration in a storage-stable surfactant-containing aqueous composition of glyphosate potassium or MEA salt is about 570 g a.e./l, this limit being a consequence of the solubility limit of the glyphosate salt in water, compounded in some cases by further limitation due to the presence of surfactant. Higher glyphosate concentrations are, of course, possible and are embraced by the present invention where the surfactant is present at only a very small concentration. However, such a low concentration of surfactant is unlikely to be agronomically useful.

Close to this upper limit of glyphosate concentration, the amount of surfactant that can be accommodated is less than at lower glyphosate concentrations. For most purposes, this small amount of surfactant is likely to be inadequate to give reliable enhancement of the herbicidal efficacy of the glyphosate to an acceptable degree. However, in certain special-purpose applications where the composition is to be diluted with a relatively small amount of water, for plant treatment at a volume of, for example, about 10 to about 50 l/ha, the surfactant concentration in a concentrate composition of the invention can usefully be as low as about 20 g/l. Such special-purpose applications include rope-wick application and ultra-low-volume aerial spraying. For general-purpose application, typically by spraying following dilution with about 50 to about 1000 l/ha, most commonly about 100 to about 400 l/ha, of water, the surfactant concentration in a concentrate composition of the invention is preferably about 60 to about 200 g/l.

In one embodiment of the invention, as shown in FIG. 2, there is provided a storage and shipping system 11a for glyphosate herbicide comprising a container illustratively in the form of a jug 12a having an illustrative capacity of 10 liters, substantially filled with an aqueous solution 13a of glyphosate, predominantly in the form of one or a mixture of the potassium and MEA salts thereof, but illustratively substantially all in the form of the MEA salt. The solution 13a has a glyphosate a.e. concentration illustratively of 46% by weight.

Also illustrated in FIG. 2 for comparison is a storage and shipping system 11b of prior art comprising a 10 liter jug 12b identical to the 10 liter jug 12a used in the system of the invention, but substantially filled with an aqueous solution 13b of the IPA salt of glyphosate at the same illustrative glyphosate a.e. concentration of 46% by weight. Glyphosate molecules 14 in both systems are indicated diagrammatically in FIG. 2 so as to provide a visual representation of the greater weight of glyphosate a.e. present in the storage and shipping system 11a of the invention.

Alternatively, as illustrated in FIG. 3, in a storage and shipping system 15a of the invention a container, illustratively a drum 16a, is smaller than the drum 16b of a storage and shipping system 15b of prior art. The drum 16a is substantially filled, to the indicated level 17a, with an aqueous solution 18a of glyphosate, illustratively substantially all in the form of the MEA salt thereof, illustratively at a glyphosate a.e. concentration of 46% by weight. The prior art drum 16b is substantially filled, to the indicated level 17b, with an aqueous solution 18b of glyphosate IPA salt at the same illustrative glyphosate a.e. concentration of 46% by weight. The volume of aqueous solution 18a contained in drum 16a is smaller than the volume of aqueous solution 18b contained in drum 16b, yet holds the same weight of glyphosate a.e., as represented by the diagrammatic representation of glyphosate molecules 14.

Further, as illustrated in FIG. 4, a larger number of such smaller containers, illustratively drums 16a by comparison with drums 16b, can be shipped in a given enclosed volume, illustratively a railroad boxcar 19, thereby enabling the shipment of a larger weight of glyphosate a.e. in a single consignment using the storage and shipping system of the invention.

As a further aspect of the present invention, a particular class of surfactants has been identified wherein compatibility with glyphosate MEA salt at the concentrations given above is unexpectedly high. Accordingly, an embodiment of the invention is a storage and shipping system for glyphosate herbicide comprising a container having a capacity of about 0.1 to about 100,000 liters or more, partially or completely filled, and preferably substantially filled, with a surfactant-containing aqueous glyphosate MEA salt solution as described above wherein the surfactant component predominantly comprises one or more surfactants each having a molecular structure comprising:

(1) a hydrophobic moiety having one or a plurality of independently saturated or unsaturated, branched or unbranched, aliphatic, alicyclic or aromatic $C_{3-18}$ hydrocarbyl or hydrocarbylidene groups joined together by 0 to about 7 linkages selected from ether, thioether, sulfoxide, ester, thioester and amide linkages, this hydrophobic moiety having in total a number J of carbon atoms where J is about 8 to about 24; and (2) a hydrophilic moiety comprising:
(i) an amino group that is cationic or that can be protonated to become cationic, having attached directly thereto 0 to 3 oxyethylene groups or polyoxyethylene chains, these oxyethylene groups and polyoxyethylene chains comprising on average no more than a number E of oxyethylene units per surfactant molecule such that E+J=25; and/or
(ii) a glycoside or polyglycoside group comprising on average no more than about 2 glycoside units per surfactant molecule.

In such surfactants the hydrophobic moiety is attached to the hydrophilic moiety in one of the following ways: (a) directly to an amino group if present, (b) by an ether linkage incorporating an oxygen atom of one of the oxyethylene groups if present or of a terminal oxyethylene unit of one of the polyoxyethylene chains if present, or (c) by an ether linkage to one of the glycoside units if present.

In the context of surfactant content, the expression "predominantly comprises" means that at least about 50%, preferably at least about 75% and more preferably at least about 90%, by weight of the surfactant component is made up of surfactants having the specified features of molecular structure. For the present purpose, the weight or concentration of surfactant component as defined herein does not include essentially non-surfactant compounds that are sometimes introduced with the surfactant component, such as water, isopropanol or other solvents, or glycols (such as ethylene glycol, propylene glycol, polyethylene glycol, etc.).

As further explanation of the relationship between E and J in polyoxyethylene amine surfactants, it has been found, surprisingly, that the larger the hydrophobic moiety (i.e., the higher the value of J) the fewer oxyethylene units can be present (i.e., the smaller is the value of E) for adequate compatibility with glyphosate MBA salt. For example, where J has an average value of about 18, as for example in a polyoxyethylene tallowamine, E, the maximum number of oxyethylene units, is about 7. However, where J has an average value of about 12, as in a polyoxyethylene cocoamine, E is about 13.

Without in any way limiting the scope of the present invention, two subclasses of surfactant, defined by formulas (V) and (VI) below, are particularly useful in storage and shipping systems of the invention.

In one embodiment of the invention, glyphosate is present in the solution predominantly in the form of the MEA salt, and the solution further contains about 20 to about 200 grams per liter of a surfactant component predominantly comprising one or more surfactants having, at a pH level of about 4, the formula

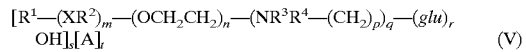

where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 8, the total number of carbon atoms in $R^1$—$(XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a unit of formula

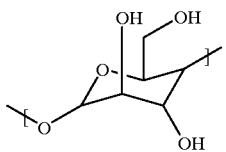

(referred to herein as a glucoside unit), r is an average number from 1 to about 2, A is an anionic entity, and s is an integer from 1 to 3 and t is 0 or 1 such that electrical neutrality is maintained.

In another embodiment of the invention, the glyphosate MEA salt solution contains about 20 to about 200 grams per liter of a surfactant component predominantly comprising one or more surfactants having, at a pH level of about 4, the formula

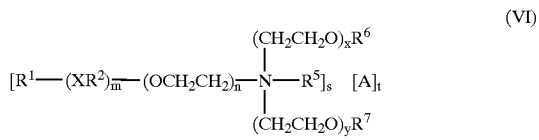

where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 9, the total number J of carbon atoms in $R^1$—$(XR^2)_m$ is about 8 to about 24, n is an average number of 0 to about 5, $R^5$ is hydrogen, $C_{1-4}$ alkyl, benzyl, an anionic oxide group or an anionic group —$(CH_2)_u C(O)O$ where u is 1 to 3, $R^6$ and $R^7$ are independently hydrogen, $C_{1-4}$ alkyl or $C_{2-4}$ acyl, x and y are average numbers such that x+y+n is not greater than the number E as defined above, A is an anionic entity and s is an integer from 1 to 3 and t is 0 or 1 such that electrical neutrality is maintained.

Surfactants conforming to formulas (V) or (VI) above include non-restrictively those that can be described as alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines, alkylamidopropylamines and the like, where the average number of oxyethylene units, if present, per surfactant molecule is no greater than 25-J where J is as defined above, and the average number of glucose units, if present, per surfactant molecule is no greater than about 2. The term "alkyl" as used in this paragraph reflects common usage in the art and means $C_{8-18}$ aliphatic, saturated or unsaturated, linear or branched hydrocarbyl.

When a maximum or minimum "average number" is recited herein with reference to a structural feature of a surfactant such as oxyethylene units or glucoside units, it is to be understood that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Illustrative surfactant types that have been found useful in systems of the invention include the following:

(A) Surfactants corresponding to formula (V) where $R^1$ is a $C_{8-18}$ aliphatic, saturated or unsaturated, linear or branched hydrocarbyl chain, m, n and q are 0, s is 1 and t is 0. This group includes several commercial surfactants collectively known in the art or referred to herein as "alkyl polyglucosides" or "APGs". Suitable examples are sold by Henkel as Agrimul™ PG-2069 and Agrimul™ PG-2076.

(B) Surfactants corresponding to formula (VI) where $R^1$ is a $C_{8-18}$ aliphatic, saturated or unsaturated, linear or branched hydrocarbyl chain and m is 0. In this group $R^1$ alone forms the hydrophobic moiety of the surfactant and is attached directly to the amino function, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include:

(B-1) Surfactants wherein x and y are 0, $R^5$ and $R^6$ are independently $C_{1-4}$ alkyl, $R^7$ is hydrogen and t is 1. This subtype includes (where $R^5$ and $R^6$ are each methyl) several commercial surfactants known in the art or referred to herein as "alkyldimethylamines". Suitable examples are dodecyldimethylamine, available for example from Akzo as Armeen™ DM12D, and cocodimethylamine and tallowdimethylamine, available for example from Ceca as Noram™ DMC D and Noram™ DMS D respectively. Such surfactants are generally provided in non-protonated form, the anion A not being supplied with the surfactant. However, in a glyphosate MEA salt formulation at a pH of about 4–5, the surfactant will be protonated and it will be recognized that the anion A can be glyphosate, which is capable of forming dibasic salts.

(B-2) Surfactants wherein x and y are 0, $R^5$, $R^6$ and $R^7$ are independently $C_{1-4}$ alkyl and t is 1. This subtype includes (where $R^5$, $R^6$ and $R^7$ are each methyl and A is a chloride ion) several commercial surfactants known in the art or referred to herein as "alkyltrimethylammonium chlorides". A suitable example is cocoalkyl trimethylammonium chloride, available for example from Akzo as Arquad™ C.

(B-3) Surfactants wherein x+y is 2 or greater, $R^6$ and $R^7$ are hydrogen and t is 1. This subtype includes commercial surfactants known in the art or referred to herein as "polyoxyethylene alkylamines" (where n is 0 and $R^5$ is hydrogen), certain "polyoxyethylene alkyletheramines" (where n is 1–5 and $R^5$ is hydrogen), "polyoxyethylene N-methyl alkylammonium chlorides" (where n is 0 and $R^5$ is methyl), and certain "polyoxyethylene N-methyl alkyletherammonium chlorides" (where n is 1–5 and $R^5$ is methyl). Suitable examples are polyoxyethylene (2) cocoamine, polyoxyethylene (5) tallowamine and polyoxyethylene (10) cocoamine, available for example from Akzo as Ethomeen™ C/12, Ethomeen™ T/15 and Ethomeen™ C/20 respectively; a surfactant conforming, when its amine group is non-protonated, to the formula

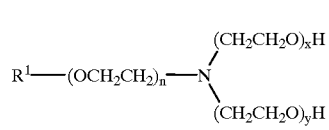

(VII)

where $R^1$ is $C_{12-15}$ alkyl and x+y is 5, as disclosed in U.S. Pat. No. 5,750,468; and polyoxyethylene (2) N-methyl cocoammonium chloride and polyoxyethylene (2) N-methyl stearylammonium chloride, available for example from Akzo as Ethoquad™ C/12 and Ethoquad™ 18/12 respectively. In cases where $R^5$ is hydrogen, i.e., in tertiary as opposed to quaternary ammonium surfactants, the anion A is typically not supplied with the surfactant. However, in a glyphosate MEA salt formulation at a pH of about 4–5, it will be recognized that the anion A can be glyphosate, which is capable of forming dibasic salts.

(B-4) Surfactants wherein $R^5$ is an anionic oxide group and t is 0. This subtype includes commercial surfactants known in the art or referred to herein as "alkyldimethylamine oxides" (where n, x and y are 0, and $R^6$ and $R^7$ are methyl), certain "alkyletherdimethylamine oxides" (where n is 1–5, x and y are 0, and $R^6$ and $R^7$ are methyl), "polyoxyethylene alkylamine oxides" (where n is 0, x+y is 2 or greater, and $R^6$ and $R^7$ are hydrogen), and certain "polyoxyethylene alkyletheramine oxides" (where n is 1–5, x+y is 2 or greater, and and $R^6$ and $R^7$ are hydrogen). Suitable examples are cocodimethylamine oxide, sold by Akzo as Aromox™ DMC, and polyoxyethylene (2) cocoamine oxide, sold by Akzo as Aromox™ C/12.

(B-5) Surfactants wherein $R^5$ is an anionic group —$CH_2C(O)O$ (acetate), x and y are 0 and t is 0. This subtype includes commercial surfactants known in the art or referred to herein as "alkylbetaines" (where n is 0, $R^5$ is acetate and $R^6$ and $R^7$ are methyl) and certain "alkyletherbetaines" (where n is 1–5, $R^5$ is acetate and $R^6$ and $R^7$ are methyl). A suitable example is cocobetaine, sold for example by Henkel as Velvetex™ AB-45.

(C) Surfactants corresponding to formula (VI) where $R^1$ is a $C_{8-18}$ aliphatic, saturated or unsaturated, linear or branched hydrocarbyl chain, m is 1, X is an ether linkage, $R^2$ is n-propylene and n is 0. In this group $R^1$ together with $OR^2$ forms the hydrophobic moiety of the surfactant which is attached directly by the $R^2$ linkage to the amino function. These surfactants are a subclass of alkyletheramines as disclosed in U.S. Pat. No. 5,750,468. Illustrative subtypes have the different hydrophilic moieties exemplified in (B-1) to (B-5) above. Suitable examples are a surfactant conforming, when its amine group is non-protonated, to the formula

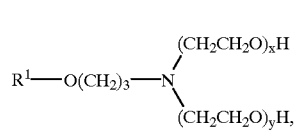

(VIII)

a surfactant conforming to the formula

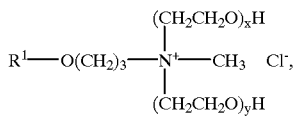

(IX)

and a surfactant conforming to the formula

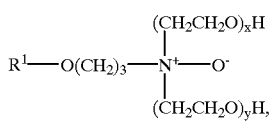

(X)

where, in each of formulas (VIII), (IX) and (X), $R^1$ is $C_{12-15}$ alkyl and x+y is 5, as disclosed in U.S. Pat. No. 5,750,468.

(D) Surfactants corresponding to formula (VI) where $R^1$ is a $C_{8-18}$ aliphatic, saturated or unsaturated, linear or branched hydrocarbyl chain, m is 1–5, each $XR^2$ is a group —OCH(CH$_3$)CH$_2$— and n is 0. In this group $R^1$ together with the —OCH(CH$_3$)CH$_2$— groups forms the hydrophobic moiety of the surfactant which is attached directly to the amino function. These surfactants are a further subclass of alkyletheramines as disclosed in U.S. Pat. No. 5,750,468. Illustrative subtypes have the different hydrophilic moieties exemplified in (B-1) to (B-5) above. A suitable example is a surfactant conforming, when its amine group is non-protonated, to the formula

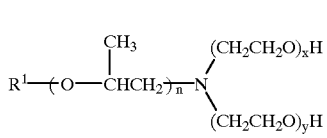

(XI)

where $R^1$ is $C_{12-15}$ alkyl, m is 2 and x+y is 5 as disclosed in U.S. Pat. No. 5,750,468.

(E) Surfactants corresponding to formula (VI) where $R^1$ is a $C_{8-18}$ aliphatic, saturated or unsaturated, linear or branched hydrocarbyl chain, m is 1, X is an amide linkage, R is n-propylene and n is 0. In this group $R^1$ together with $XR^2$ forms the hydrophobic moiety of the surfactant which is attached directly by the $R^2$ linkage to the amino function. In preferred surfactants of this group, x and y are 0, $R^5$ is hydrogen or $C_{1-4}$ alkyl, $R^6$ and $R^7$ are independently $C_{1-4}$ alkyl and t is 1. A suitable example is cocoamidopropyl dimethylamine propionate, sold for example by McIntyre as Mackalene™ 117.

(F) Surfactants corresponding to formula (VI) where $R^1$ is hydrogen, m is 3–8 and each $XR^2$ is a group —OCH(CH$_3$)CH$_2$—. In this group the polyether chain of —OCH(CH$_3$)CH$_2$— groups (a polyoxypropylene chain) forms the hydrophobic moiety of the surfactant which is linked directly or via one or more oxyethylene units to the amino function. In preferred surfactants of this group, x and y are 0, $R^5$, $R^6$ and $R^7$ are independently $C_{1-4}$ alkyl and t is 1. These surfactants are a subclass of the polyoxypropylene quaternary ammonium surfactants disclosed in U.S. Pat. No. 5,652,197. In a suitable example, m is 7, n is 1, $R^5$, $R^6$ and $R^7$ are each methyl, and A is chloride.

In surfactants where t is 1, A can be any suitable anion but preferably is chloride, bromide, iodide, sulfate, ethosulfate, phosphate, acetate, propionate, succinate, lactate, citrate or tartrate, or, as indicated above, glyphosate.

In one embodiment of the invention the aqueous solution contains a surfactant of a class of alkyletheramines disclosed in U.S. Pat. No. 5,750,468. In a further embodiment, surfactants present are other than alkyletheramines as disclosed in U.S. Pat. No. 5,750,468.

A particular embodiment of the invention employs a glyphosate MEA salt composition as described above wherein the glyphosate concentration, expressed in g a.e./l, is higher than the maximum concentration that would provide acceptable storage-stability if all the glyphosate were instead present as the IPA salt. Again, by acceptable storage-stability is meant exhibiting no phase separation at temperatures of about 50° C. or lower, and exhibiting substantially no formation of crystals of glyphosate or salt thereof when exposed to temperatures not lower than about 0° C. for a period of up to about 7 days.

Another particular embodiment of the invention employs a glyphosate MEA salt composition as described above having lower viscosity than an otherwise similar composition wherein all the glyphosate is instead in the form of the IPA salt. It is particularly useful if the lower viscosity is manifested as improved pourability and/or pumpability at low temperatures, for example about –10° C. to about 10° C. It has been discovered, surprisingly, that reduced viscosity is a feature of virtually all aqueous concentrate compositions of glyphosate MEA salt, when compared with corresponding compositions of glyphosate IPA salt. This discovery is especially well illustrated by Example 4 herein, and in particular by the data in Table 6 forming part of that Example.

Where, in an aqueous concentrate composition, the concentration of glyphosate salt and/or the concentration of surfactant are so high that viscosity is unacceptably high even with the MEA salt, the MEA salt nonetheless provides a significant advantage over the IPA salt. In such a composition, addition of a small amount of water typically lowers the viscosity to a much greater degree when the glyphosate is present as the MEA salt rather than the IPA salt. The amount of water required to lower viscosity to any desired level is significantly less in the case of the MEA salt than in the case of the IPA salt.

It has unexpectedly been found that replacement of glyphosate IPA salt by glyphosate MEA salt in a surfactant-containing aqueous solution concentrate composition can provide a further benefit in the form of reduced irritancy to eyes. This is especially surprising as it is known that it is the surfactant component of such compositions, especially where the predominant surfactant is an amine-based surfactant, that is primarily responsible for any eye irritancy exhibited. Accordingly, a storage and shipping system of the invention can have the further benefit that hazard from spillage or leakage during handling of the system is reduced by comparison with prior art storage and shipping systems using glyphosate IPA salt.

Although the present invention is directed primarily at storage and shipping systems employing concentrated aqueous solutions of the MEA salt of glyphosate, one or more additional herbicidal active ingredients can optionally be present, including without restriction water-soluble forms of acifluorfen, asulam, benazolin, bentazon, bialaphos, bispyribac, bromacil, bromoxynil, carfentrazone, chloramben, clopyralid, 2,4-D, 2,4-DB, dalapon, dicamba, dichlorprop, diclofop, difenzoquat, diquat, endothall, fenac, fenoxaprop, flamprop, fluazifop, fluoroglycofen, fluroxypyr, fomesafen, fosamine, glufosinate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, sulfamic acid, 2,3,6-TBA, TCA and triclopyr. Where the additional herbicide is anionic, like glyphosate, it is preferred that the additional herbicide is likewise present predominantly as the MEA salt.

An embodiment of the invention therefore is a storage and shipping system for two or more anionic herbicides, one of which is glyphosate, comprising a container having a capacity of about 0.1 to about 100,000 liters, partially or completely filled, and preferably substantially filled, with an aqueous solution comprising glyphosate predominantly in the form of the MEA salt thereof, and a second anionic herbicide predominantly in the form of the MEA salt thereof, the total concentration of the glyphosate and the second anionic herbicide together being about 360 to about 600 g a.e./l, the solution preferably further comprising a surfactant component, selected in accordance with the invention, dissolved or in stable dispersion therein at a concentration of about 20 to about 200 g/l.

In this embodiment, it is preferred that the weight/weight ratio of glyphosate to the second anionic herbicide be not less than about 1:1, for example from about 1:1 to about 30:1. The second anionic herbicide is preferably selected from the group consisting of acifluorfen, bialaphos, carfentrazone, clopyralid, 2,4-D, 2,4-DB, dicamba, dichlorprop, glufosinate, MCPA, MCPB, mecoprop, methylarsonic acid, nonanoic acid, picloram, triclopyr and herbicides of the imidazolinone class, including imazameth, imazamethabenz, imazamox, imazapic, imazapyr, imazaquin and imazethapyr.

Also embraced by the present invention are storage and shipping systems employing liquid concentrate formulations having an aqueous phase containing the MEA salt of glyphosate and a non-aqueous phase optionally containing a second herbicidal active ingredient that is relatively water-insoluble. Such formulations illustratively include emulsions (including macro- and microemulsions, water-in-oil, oil-in-water and water-in-oil-in-water types), suspensions and suspoemulsions. The non-aqueous phase can optionally comprise a microencapsulated component, for example a microencapsulated herbicide. In formulations of the invention having a non-aqueous phase, the concentration of glyphosate a.e. in the composition as a whole is nonetheless within the ranges recited herein for aqueous solution concentrate formulations.

Illustrative water-insoluble herbicides that can be used in such formulations include acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlomitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate. It is preferred that the weight/weight ratio of glyphosate a.e. to such water-insoluble herbicide be not less than 1:1, for example from about 1:1 to about 30:1.

Excipient ingredients other than the above-defined surfactant component can optionally be present in a composition useful in a system of the invention, so long as the composition is storage-stable as defined herein. Such additional excipient ingredients include conventional formulation additives such as dyes, thickeners, crystallization inhibitors, antifreeze agents including glycols, foam moderating agents, antidrift agents, compatibilizing agents, etc.

A type of excipient ingredient often used in glyphosate formulations is an inorganic salt such as ammonium sulfate, included to enhance herbicidal activity, or consistency of herbicidal activity, of the glyphosate. As the content of inorganic salt in the formulation needed to provide such enhancement is typically relatively high, often greater than the amount of glyphosate present, it will seldom be useful to add such salt to a composition to be employed in a system of the invention. The amount of ammonium sulfate, for example, that could be accommodated in a storage-stable aqueous composition containing glyphosate MEA salt at a concentration of at least 360 g a.e./l would be so small as to bring no substantial benefit. An alternative, therefore, is to include a small amount of a synergist such as an anthraquinone compound or a phenyl-substituted olefin compound as disclosed in International Publication Nos. WO 98/33384 and WO 98/33385 respectively.

A container useful in a storage and shipping system for glyphosate herbicide according to the present invention can be any known container useful for storing and shipping glyphosate IPA salt, constructed of materials that can safely and conveniently be used in prolonged contact with a concentrated glyphosate salt solution having a pH of about 4–5. A preferred material of construction is HDPE or, particularly for large bulk tanks, stainless steel.

Illustratively, the container can be a single-use jug or flask having a capacity of about 0.1 to about 10 liters, a drum having a capacity of about 50 to about 200 liters, a shuttle having a capacity of about 200 to about 2000 liters, a modular bulk shipping tank having a capacity of about 15,000 to about 20,000 liters, a tank of a tank truck having a capacity of about 20,000 to about 25,000 liters, or a railcar tank having a capacity of about 75,000 to about 90,000 liters.

Small single-use containers have an aperture covered by a removable cap, for example a screw-cap, and can be molded in such a way as to provide a pouring spout. Such a container is preferably designed in a way known in the art to minimize spilling, for example by permitting continuous entry of air to replace the liquid as it is poured so as to avoid "glugging". Large capacity containers, for example those having a capacity greater than about 50 liters, can have a spigot for withdrawing the liquid composition held within, and/or a connection for a pump to permit rapid transfer of the composition. In a particular embodiment, the container is provided with an integral pump.

The present invention can also be described as a method of storing or transporting a glyphosate herbicide.

Thus, in one embodiment, a method of storing a glyphosate herbicide is provided, comprising four steps.

In the first step, glyphosate acid is reacted in an aqueous medium with a base that provides potassium or monoethanolammonium cations, to form an aqueous solution of the monobasic potassium or monoethanolammonium salt of glyphosate. Preferably the base is potassium hydroxide or monoethanolamine, most preferably the latter. Approximately equimolar amounts of glyphosate and this base are used.

In the second step, the aqueous solution is adjusted if necessary with water and/or other ingredients to form an adjusted solution having a glyphosate acid equivalent concentration between about 30 percent by weight and a maximum percent by weight dictated by the solubility of the salt. Normally adjustment is done with water only, but if desired other ingredients, including surfactant, can be added at this stage. Where the salt is the monoethanolammonium salt of glyphosate, the solution is preferably adjusted to a glyphosate acid equivalent concentration of about 30 to about 46 percent by weight, more preferably about 40 to about 46 percent by weight.

In the third step, a container having a capacity of about 0.1 to about 100,000 liters or more is substantially filled with the adjusted solution.

In the fourth step, the filled container is placed in a suitable storage location. This can be a warehouse or equivalent storage facility.

In another embodiment, a method of transporting a glyphosate herbicide is provided, comprising five steps. The first and second steps are exactly as described immediately above.

In the third step, a multiplicity of containers each having a capacity of about 0.1 to about 2000 liters are each substantially filled with the adjusted solution. The containers are, for example, single-use containers such as jugs, flasks or drums, or are refillable containers such as shuttles.

In the fourth step, the filled containers are loaded into an enclosed volume in or on a road or rail vehicle or water-borne vessel in a loading location. The enclosed volume is, for example, that of a modular box container adapted for road, rail and water transportation, a truck or a railroad boxcar.

In the fifth step, the vehicle or vessel, after loading of the enclosed volume, is caused to move from the loading location to an unloading location.

In a further embodiment another method of transporting a glyphosate herbicide is provided, comprising five steps. The first and second steps are exactly as described above.

In the third step, a bulk container having a capacity of about 15,000 to about 100,000 liters or more is substantially filled with the adjusted solution. The bulk container is, for example, a modular bulk shipping tank, or the tank of a tank truck or railcar.

In the fourth step, which can occur before or after any of the first three steps, the bulk container is secured in or on a road or rail vehicle or water-borne vessel in a loading location. In the case of a tank truck or a railcar the bulk container can be an integral part of the vehicle and is secured thereto at the time of assembling the vehicle.

In the fifth step, the vehicle or vessel, after loading and securing of the bulk container, is caused to move from the loading location to an unloading location.

EXAMPLES

The following Examples are provided for illustrative purposes only and are not intended to limit the scope of the present invention. The Examples will permit better understanding of the invention and perception of its advantages and certain variations of execution.

Example 1

In a 1 liter glass vessel with magnetic stirrer are mixed 479.2 g glyphosate acid, technical grade (assay 96%), 166.0 g monoethanolamine and water to 1000 g. Reaction of the glyphosate acid with the monoethanolamine to form the MEA salt of glyphosate is exothermic. The reaction mixture is allowed to cool to room temperature. The specific gravity (20/15.6° C.) of the resulting 62.6% by weight aqueous solution of glyphosate MEA salt, containing 46.0% by weight glyphosate a.e., is measured and found to be 1.32. The density of the solution at 25° C. is 1.31 g/l, thus the volume at 25° C. of 1000 g of this solution is 763 ml and the weight/volume concentration of glyphosate is 602 g a.e./l.

For comparison, a 62.1% by weight aqueous solution of glyphosate IPA salt, also containing 46.0% by weight glyphosate a.e., is found to have a specific gravity of 1.24. The density of the solution at 25° C. is 1.23 g/l, thus the volume at 25° C. of 1000 g of this comparative solution is 813 ml and the weight/volume concentration of glyphosate is 565 g a.e./l.

A first 100 ml flask is filled at 25° C. with the glyphosate MEA salt solution of this Example and a second 100 ml flask with the comparative glyphosate IPA salt solution just described. The first flask is found to contain 60.2 grams of glyphosate a.e., whereas the second flask is found to contain only 56.5 grams of glyphosate a.e.; in other words the first flask, representative of the present invention, contains approximately 6.5% more glyphosate a.e. than the second flask.

Example 2

A series of aqueous solutions of glyphosate MEA salt, having a range of glyphosate a.e. concentrations, are prepared by the general procedure of Example 1. Specific gravity is measured for each solution.

Figure 1:
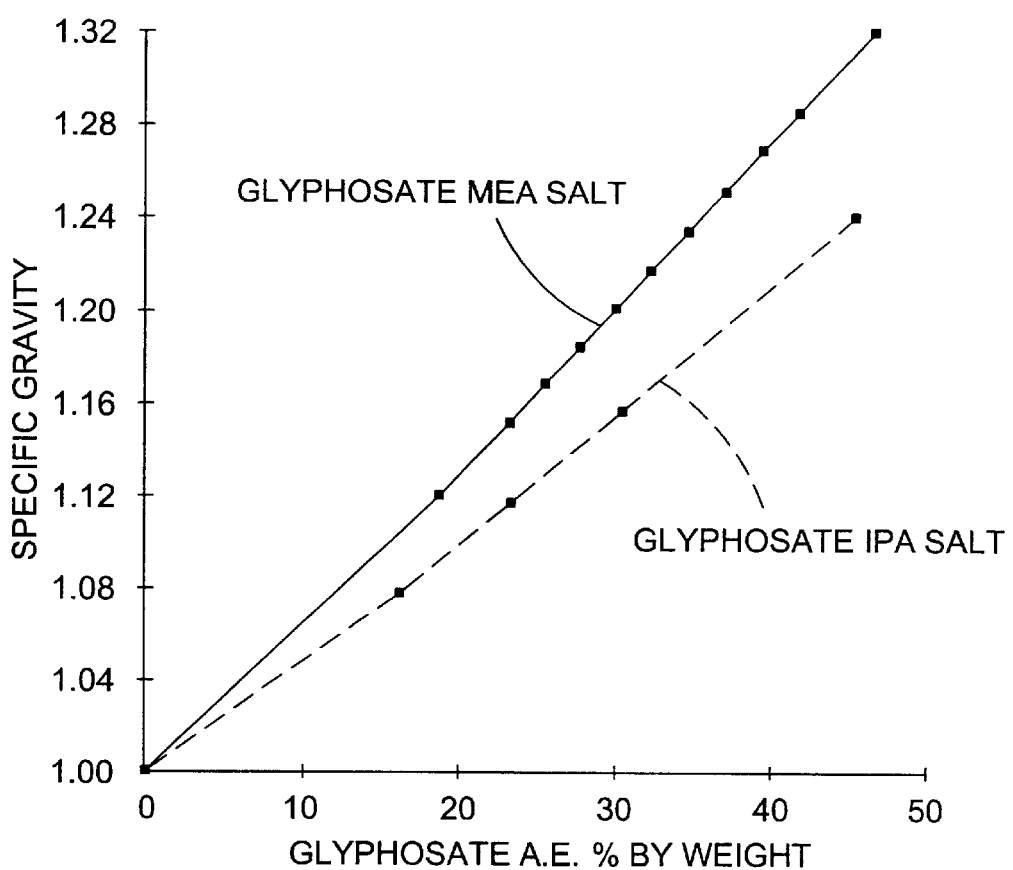
FIG. 1 is a graphical representation comparing, for glyphosate IPA and MEA salts, the relationship between weight percent concentration of glyphosate a.e. in an aqueous solution of the salt and the specific gravity of the aqueous solution.

Results are shown in FIG. 1, by comparison with solutions of glyphosate IPA salt. At all concentrations, specific gravity of the MEA salt solution is found to be significantly higher than that of the corresponding IPA salt solution.

Glyphosate MEA salt solution of this Example having a glyphosate concentration of 29.9% a.e. by weight is added in sufficient volume to a 10 liter jug normally used commercially for storage and shipping of glyphosate IPA salt solution at 30.2%, to substantially fill that container. The resulting filled container is a storage and shipping system in accordance with the present invention. By virtue of the fact that the 29.9% a.e. by weight glyphosate MEA salt solution has a specific gravity of 1.1991, which is 3.7% higher than that of the 30.2% glyphosate IPA salt solution (specific gravity 1.1566), the filled container of the invention holds 3585 grams of glyphosate a.e., compared with 3493 grams of glyphosate a.e. in a commercial storage and shipping system consisting of an identical container filled instead with glyphosate IPA salt solution.

Example 3

The 46% a.e. by weight aqueous glyphosate MEA salt solution of Example 1 is reprepared in larger volume.

A cylindrical HDPE drum is fabricated identical to a 100 liter drum used commercially for storage and shipping of 46% a.e. by weight glyphosate IPA salt solution, except that the diameter of the drum is 2.55% smaller than that of the commercial drum, so that its cross-sectional area is 6.5% less. The capacity of the smaller drum is 93.5 liters. This 93.5 liter drum is substantially filled with the glyphosate MEA salt solution to form a storage and shipping system of the present invention. The net weight of the filled 93.5 liter drum of the invention is equal to that of a 100 liter drum filled with 46% a.e. by weight glyphosate IPA salt solution. However, the smaller diameter of the 93.5 liter drum enables a larger number of such drums to be stored in a warehouse of given dimensions, or shipped for example in a freight compartment of given dimensions in a seagoing vessel or in an aircraft.

Filling of the drum to create the storage and shipping system of the invention takes less time, and thereby costs less, than filling of a 100 liter drum with 46% a.e. glyphosate IPA salt solution, for two reasons: (1) filling time is related to volume, which is 6.5% less in the case of the 93.5 liter drum of the invention; and (2) the MEA salt solution has much lower viscosity (88 cPs at 25° C.) than the IPA salt solution (165 cPs at 25° C.), enabling greater flow rate.

The filled drum of the invention is, in addition, more ergonomically efficient for the ultimate user than the 100 liter drum of IPA salt solution. First, its smaller diameter makes it easier to handle and lift, even though the weight is no less. Second, the low viscosity of the MEA salt solution enables faster and easier pouring or pumping of the solution from the drum into, for example, the tank of a sprayer. Third, the low viscosity of the MEA salt solution results in the drum being easier and quicker to rinse when empty. This in turn prevents waste and helps ensure chemical-free disposal, return or recycle of the empty drum. The viscosity advantage of the MEA salt solution over the IPA salt solution is magnified at lower temperatures.

Example 4

Surfactant-containing compositions 4-01 to 4-11 are prepared as described below. Each contains glyphosate MEA salt, and is prepared using a 46% a.e. by weight, 602 g a.e./l aqueous solution thereof prepared as in Example 1. The surfactant in each case is selected from the list provided in Table 2 below. Comparative compositions are prepared with glyphosate IPA salt, which is added as a 46% a.e. by weight, 565 g a.e./l aqueous solution thereof as described in Example 1.

TABLE 2

Surfactants used in compositions of Example 4.

| Surfactant | Chemical description | Trade name and supplier |
|---|---|---|
| A | polyoxyethylene (5) cocoamine | Ethomeen ™ C/15 (Akzo) |
| B | N-cocoalkyl-N-methyl-N,N-diethanolammonium chloride | Ethoquad C/12-W (Akzo) |
| C | N-cocoalkyl-N,N-diethanolamine oxide | Aromox ™ C/12 (Akzo) |
| D | compound of formula (VIII) where $R^1$ is isotridecyl and $x + y = 5$ | E-17-5 (Tomah) |
| E | compound of formula (IX) where $R^1$ is isodecyl and $x + y = 2$ | Q-14-2 (Tomah) |
| F | compound of formula (XI) where $R^1$ is $C_{12-14}$ alkyl, $n = 2$ and $x + y = 5$ | not commercially available* |

*A method of making this surfactant is disclosed in United Kingdom Patent No. 1,588,079

Target weight/volume concentrations, expressed below in the format [glyphosate a.e.]/[surfactant], the units being g/l, are established. Actual weight/volume concentrations can differ slightly from target concentrations because the ingredients are measured by weight for convenience. Amounts of ingredients mixed to provide the various target concentrations are as shown in Table 3 (for glyphosate MEA salt compositions of the invention) and Table 4 (for comparative glyphosate IPA salt compositions).

TABLE 3

Amounts of ingredients used in preparing glyphosate MEA salt compositions of Example 4.

| Target weight/volume concentrations (g/l) | 46% MEA salt solution (g) | Surfactant (g) | Water (g) |
|---|---|---|---|
| 490/100 | 82.94 | 8.00 | 9.06 |
| 480/120 | 81.24 | 10.00 | 8.76 |
| 480/80 | 81.45 | 6.40 | 12.15 |
| 480/60 | 81.45 | 4.80 | 13.75 |
| 445/110 | 76.46 | 8.86 | 14.68 |

TABLE 4

Amounts of ingredients used in preparing comparative glyphosate IPA salt compositions of Example 4.

| Target weight/volume concentrations (g/l) | 46% IPA salt solution (g) | Surfactant (g) | Water (g) |
|---|---|---|---|
| 490/100 | 90.01 | 8.30 | 0.79 |
| 480/120 | 88.69 | 10.00 | 1.31 |
| 480/80 | 88.69 | 6.70 | 4.61 |
| 480/60 | 88.69 | 5.00 | 6.31 |
| 445/110 | 81.00 | 9.20 | 9.80 |

Specific gravity (20/15.6° C.), viscosity at 25° C. and cloud point are recorded for each composition prepared as shown in Table 5. Cloud point is a measure of the maximum temperature at which a given aqueous composition containing a surfactant and a salt at defined concentrations forms a single-phase solution. Above the cloud point, the surfactant separates from the solution, initially as a hazy or cloudy dispersion, and, upon standing, as a distinct phase generally rising to the surface of the solution. Cloud point is determined by heating the composition until the solution becomes cloudy, and then allowing the composition to cool, with agitation, while its temperature is continuously monitored. A temperature reading taken when the solution clears is a measure of cloud point.

TABLE 5

Data on compositions of Example 4.

| Composition no. | Target concentrations | Surfactant | Glyphosate salt | Specific gravity | Viscosity at 25° C. (cPs) | Cloud point (° C.) |
|---|---|---|---|---|---|---|
| 4-01 | 480/120 | A | MEA | 1.2561 | 73 | >95 |
|  |  |  | IPA | 1.2100 | 474 | >95 |
| 4-02 | 480/120 | B | MEA | 1.2601 | 35 | >95 |
|  |  |  | IPA | 1.2096 | 126 | >95 |
| 4-03 | 480/120 | C | MEA | 1.2509 | 128 | 55 |
|  |  |  | IPA | 1.1989 | 259 | >95 |
| 4-04 | 480/120 | D | MEA | 1.2613 | 329 | 82 |
|  |  |  | IPA | 1.2098 | 461 | 88 |
| 4-05 | 445/110 | D | MEA | 1.2349 | 70 | 73 |
|  |  |  | IPA | 1.1899 | 210 | 92 |
| 4-06 | 480/120 | E | MEA | 1.2479 | 217 | >95 |
|  |  |  | IPA | 1.2041 | 448 | >95 |
| 4-07 | 490/100 | F | MEA | 1.2655 | 83 | 71 |
|  |  |  | IPA | 1.2152 | 349 | 78 |
| 4-08 | 480/120 | F | MEA | 1.2593 | 93 | 70 |
|  |  |  | IPA | 1.2078 | 382 | 79 |
| 4-09 | 480/80 | F | MEA | 1.2574 | 54 | 71 |
|  |  |  | IPA | 1.2105 | 185 | 76 |
| 4-10 | 480/60 | F | MEA | 1.2613 | 45 | 70 |
|  |  |  | IPA | 1.2098 | 132 | 85 |
| 4-11 | 445/110 | F | MEA | 1.2438 | 49 | >95 |
|  |  |  | IPA | 1.1939 | 157 | 81 |

It will be noted in Table 5 that all compositions of the invention containing glyphosate MEA salt have significantly lower viscosity than corresponding IPA salt compositions. The magnitude of this viscosity advantage in favor of the MEA salt compositions depends to some extent on the choice and concentration of surfactant. For example, composition 4-01 of the invention, having target concentrations of 480 g/l glyphosate a.e. in the form of MEA salt and 120 g/l polyoxyethylene (5) cocoamine surfactant, exhibits an especially great advantage over the comparative IPA salt composition.

In some but not all cases illustrated in Table 5, a glyphosate MEA salt composition exhibits a lower cloud point than the corresponding IPA salt composition. However, in none of these cases is the cloud point lower than 50° C., and in only one case (composition 4-03) does cloud point approach this lower limit of commercial acceptability. Thus, in general, where a reduction in cloud point occurs with replacement of IPA salt by MEA salt, this reduction is an acceptable trade-off for the major advantage in viscosity, and thus in pouring and pumping behavior, enabled by such replacement.

Glyphosate MEA salt compositions 4-01 to 4-11 are reprepared in larger volume and 10 liter jugs are substantially filled with these compositions to create, in each case, a storage and shipping system of the invention.

Example 5

The maximum surfactant concentration attainable in practice in an aqueous concentrate composition containing glyphosate salt at 540 g a.e./l is compared for MEA and IPA salts. This is determined by adding a selected surfactant in increments to a 46% a.e. by weight aqueous solution of the glyphosate salt until the glyphosate weight/volume concentration falls from its initial level (565 g a.e./l for IPA salt, 602 g a.e./l for MEA salt) to 540 g a.e./l. The study is conducted using either Surfactant A or Surfactant F of Table 3 above.

When the maximum attainable surfactant concentration is reached, viscosity is measured at 25° C. Results are shown in Table 6. Note that a composition having the maximum attainable surfactant concentration as determined by this procedure does not necessarily exhibit acceptable stability as measured by cloud point and/or crystal formation.

TABLE 6

Maximum attainable surfactant concentration in an aqueous concentrate composition having 540 g/l glyphosate a.e. concentration.

| Glyphosate salt | Surfactant | Maximum attainable surfactant concentration (g/l) | Viscosity at 25° C. (cPs) |
|---|---|---|---|
| MEA | A | 116 | 210 |
| IPA | A | 46 | 384 |
| MEA | F | 119 | 210 |
| IPA | F | 46 | 362 |

The data in Table 6 illustrate one of the most beneficial advantages of glyphosate MEA salt compositions, and one of the most surprising. Using the MEA salt, it is possible to achieve, at the extremely high glyphosate a.e. concentration of 540 g a.e./l, a concentration of selected surfactant more than 2.5 times the maximum attainable using the IPA salt. This is particularly unexpected, as it has been determined that the MEA salt is much less compatible than the IPA salt with polyoxyethylene (15) tallowamine, the hitherto most widely used surfactant in glyphosate IPA salt compositions.

Using surfactants of the type now selected, it can be seen from Table 6 that with the MEA salt the surfactant/glyphosate a.e. weight ratio is greater than 1:5, a level consistent with commercially acceptable herbicidal efficacy, whereas with the IPA salt this ratio is well below 1:10. Equally importantly, the surfactants illustrated in Table 6 are known in the art to be highly effective in enhancing glyphosate herbicidal efficacy at surfactant/glyphosate a.e. ratios of 1:5 or greater (see, for example, U.S. Pat. No. 5,668,085 with regard to Surfactant A and U.S. Pat. No. 5,750,468 with regard to Surfactant F). Thus a composition that can take advantage of such surfactants, yet provide a glyphosate a.e. loading as high as 540 g a.e./l, is a significant advance in the art that could not have been predicted from prior knowledge of these surfactants or of glyphosate MEA salt.

Even more surprising is the finding, as shown in Table 6, that even with the much higher surfactant concentration attainable with the MEA salt, viscosity of the MEA salt compositions is nonetheless much lower than that of the IPA salt compositions. The IPA salt compositions have not only a low surfactant concentration unlikely to provide commercially acceptable herbicidal efficacy, especially at higher spray volumes, but also a high viscosity unlikely to permit commercially acceptable pouring or pumping behavior, especially at lower temperatures than exemplified in Table 6. By contrast, the MEA salt compositions not only can be expected to deliver good herbicidal efficacy, but also do not present a pouring or pumping problem.

Theoretically it is possible to attain slightly higher surfactant concentrations than shown in this Example by starting with a glyphosate MEA or IPA salt solution even more concentrated than 46% a.e. by weight. However, the glyphosate salt concentration of the resulting composition will then be so close to the limit of solubility that in practice the composition is unlikely to have acceptable storage-stability, and in particular is likely to exhibit deposition of crystals of glyphosate or salt thereof, particularly at low temperatures.

A 10 liter jug is substantially filled with each of the 540 g a.e./l glyphosate MEA salt compositions of this Example to create a storage and shipping system of the invention. In addition to other advantages mentioned above, this storage and shipping system has the advantage over a corresponding one containing glyphosate IPA salt at 540 g a.e./l in that the composition is "fully loaded", that is, needs no further surfactant addition by the user to deliver acceptable and reliable herbicidal effectiveness. This provides a further environmental as well as economic advantage for the user, who does not, with the storage and shipping system of the invention, have additional surfactant containers that require rinsing and disposal.

Example 6

Storage-stability at low temperature is compared for four compositions. Composition 6-01 contains glyphosate MEA salt at a concentration of 540 g a.e./l and surfactant A at 46 g/l. Composition 6-02 is similar but with surfactant F at 46 g/l. Comparative compositions are prepared in each case, using glyphosate IPA salt in place of glyphosate MEA salt, but with the same surfactants at the same concentration of 46 g/l, the maximum attainable with the IPA salt as shown in Example 5.

Compositions are placed in capped glass bottles in a refrigerated storage area at 0° C. for 3 days. A seed crystal of the same glyphosate salt as used in preparing the composition is then added, and the compositions are stored for a further 7 days. At the end of this period, the compositions are examined for crystal growth.

No crystal growth is evident for the MEA salt compositions 6-01 and 6-02, but significant crystal growth is seen in both comparative IPA salt compositions. When placed in a container to create a storage and shipping system of the invention, glyphosate MEA salt compositions 6-01 and 6-02 exhibit a significant advantage in low temperature storage-stability.

Example 7

Glyphosate MEA salt compositions 7-01 and 7-02 are prepared, substantially identical to compositions 4-08 and 4-11 respectively, and comparative IPA salt compositions are likewise prepared. Viscosity is measured at 25° C. and at a series of lower temperatures, to verify that the low viscosity advantage seen at 25° C. for MEA salt compositions continues to hold true at the lower temperatures, where in practice most pouring and pumping problems are seen. Results are shown in Table 7.

TABLE 7

Low temperature viscosity of compositions of Example 7.

| Composition no. | Target concentrations | Surf-actant | Glyphosate salt | Viscosity (cPs), at ° C. | | | | |
|---|---|---|---|---|---|---|---|---|
| | | | | 25 | 20 | 15 | 10 | 0 |
| 7-01 | 480/120 | F | MEA | 110 | 118 | 170 | 229 | 456 |
| | | | IPA | 262 | 426 | 541 | 889 | 2300 |
| 7-02 | 445/110 | F | MEA | 45 | n.d. | 69 | 104 | 180 |
| | | | IPA | 122 | n.d. | 198 | 296 | 654 | n.d. = not determined

As shown in Table 7, the low viscosity advantage of glyphosate MEA salt compositions of the invention over the corresponding IPA salt compositions becomes even more significant at lower temperatures. When placed in a container to create a storage and shipping system of the invention, glyphosate MEA salt compositions 7-01 and 7-02 exhibit all the advantages recited herein that are related to low viscosity, especially at low temperatures.

Example 8

Glyphosate MEA salt composition 8-01 is prepared, substantially identical to compositions 4-08 and 7-01, having a glyphosate concentration of 480 g a.e./l, and a glyphosate IPA salt composition having the same glyphosate concentration and the same surfactant F at the same 120 g/l concentration is prepared for comparative purposes.

A standard eye irritation test is conducted on these compositions, following U.S. Environmental Protection Agency (EPA) assessment guidelines, subsection F, *Hazard Evaluation: Human and Domestic Animals* (Revised edition, 1984), Section 81-4, *Primary Eye Irritation*. The comparative IPA salt composition is found to cause eye irritation sufficient to place that composition in the most severely irritant class (Category I) used by EPA in classifying pesticide formulations. By comparison, composition 8-01 of the invention is found to cause a lesser degree of eye irritation, placing that composition in Category II.

When placed in a container to create a storage and shipping system of the invention, glyphosate MEA salt composition 8-01 illustrates yet another advantage of the invention, namely reduced hazard to a person handling such container, especially in a situation of accidental breakage or leakage of the container.

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A method of maximizing storage efficiency for glyphosate herbicide comprising the steps of (1) selecting an aqueous solution of monobasic potassium or monoethanolammonium salt of glyphosate having a viscosity less than a similarly formulated composition of the IPA salt of glyphosate, and having a specific gravity greater than a similarly formulated composition of the IPA salt of glyphosate;

(2) adjusting said solution if necessary with water and/or other ingredients to form an adjusted solution having a glyphosate acid equivalent concentration between about 40 percent by weight and a maximum percentage by weight dictated by the solubility of said salt;

(3) substantially filling a container having a capacity of about 0.1 to about 100,000 liters or more with said adjusted solution; and (4) placing said container after filling in a suitable storage location.

2. The method of claim 1 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

3. The method of claim 2 wherein said surfactant component is selected such that the composition exhibits substantially no crystallization of said glyphosate or salt thereof when stored at a temperature not lower than about 0° C. for a period of up to about 7 days.

4. A method of maximizing storage efficiency for glyphosate herbicide comprising the steps of (1) selecting an aqueous solution of a monobasic potassium or monoethanolammonium salt of glyphosate having a viscosity less than a similarly formulated composition of the IPA salt of glyphosate, and having a specific gravity greater than a similarly formulated composition of the IPA salt of glyphosate;

(2) adjusting said solution if necessary with water and/or other ingredients to form an adjusted solution having a glyphosate acid equivalent concentration between about 40 percent by weight and a maximum percentage by weight dictated by the solubility of said salt;

(3) substantially filling a multiplicity of containers having a capacity of about 0.1 to about 2000 liters or more with said adjusted solution;

(4) loading said containers after filling into an enclosed volume in or on a road or rail vehicle or water-borne vessel in a loading location; and (5) causing said vehicle or vessel after loading to move from the loading location to an unloading location.

5. The method of claim 4 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

6. The method of claim 5 wherein said surfactant component is selected such that the composition exhibits substantially no crystallization of said glyphosate or salt thereof when stored at a temperature not lower than about 0° C. for a period of up to about 7 days.

7. A method of maximizing storage efficiency for glyphosate herbicide comprising the steps of (1) selecting an aqueous solution of a monobasic potassium or monoethanolammonium salt of glyphosate having a viscosity less than a similarly formulated composition of the IPA salt of glyphosate, and having a specific gravity greater than a similarly formulated composition of the IPA salt of glyphosate;

(2) adjusting said solution if necessary with water and/or other ingredients to form an adjusted solution having a glyphosate acid equivalent concentration between about 40 percent by weight and a maximum percentage by weight dictated by the solubility of said salt;

(3) substantially filling a bulk container having a capacity of about 15,000 to about 100,000 liters or more with said adjusted solution;

(4) securing said bulk container in or on a road or rail vehicle or water-borne vessel in a loading location; and (5) causing said vehicle or vessel after loading to move from the loading location to an unloading location.

8. The method of claim 7 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

9. The method of claim 8 wherein said surfactant component is selected such that the composition exhibits substantially no crystallization of said glyphosate or salt thereof when stored at a temperature not lower than about 0° C. for a period of up to about 7 days.

10. A method of maximizing storage efficiency for glyphosate herbicide comprising the steps of (1) selecting an aqueous solution of the monoethanolammonium salt of glyphosate having a viscosity less than a similarly formulated composition of the IPA salt of glyphosate, and having a specific gravity greater than a similarly formulated composition of the IPA salt of glyphosate;

(2) adjusting said solution if necessary with water and/or other ingredients to form an adjusted solution having a glyphosate acid equivalent concentration between about 30 percent by weight and a maximum percentage by weight dictated by the solubility of said salt;

(3) substantially filling a container having a capacity of about 0.1 to about 100,000 liters or more with said adjusted solution; and (4) placing said container after filling in a suitable storage location.

11. The method of claim 10 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

12. The method of claim 11 wherein said surfactant component is selected such that the composition exhibits substantially no crystallization of said glyphosate or salt thereof when stored at a temperature not lower than about 0° C. for a period of up to about 7 days.

13. A method of maximizing storage efficiency for glyphosate herbicide comprising the steps of (1) selecting an aqueous solution of the monoethanolammonium salt of glyphosate having a viscosity less than a similarly formulated composition of the IPA salt of glyphosate, and having a specific gravity greater than a similarly formulated composition of the IPA salt of glyphosate;

(2) adjusting said solution if necessary with water and/or other ingredients to form an adjusted solution having a glyphosate acid equivalent concentration between about 30 percent by weight and a maximum percentage by weight dictated by the solubility of said salt;

(3) substantially filling a multiplicity of containers having a capacity of about 0.1 to about 2000 liters or more with said adjusted solution;

(4) loading said containers after filling into an enclosed volume in or on a road or rail vehicle or water-borne vessel in a loading location; and (5) causing said vehicle or vessel after loading to move from the loading location to an unloading location.

14. The method of claim 13 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

15. The method of claim 14 wherein said surfactant component is selected such that the composition exhibits substantially no crystallization of said glyphosate or salt thereof when stored at a temperature not lower than about 0° C. for a period of up to about 7 days.

16. A method of maximizing storage efficiency for glyphosate herbicide comprising the steps of
(1) selecting an aqueous solution of the monoethanolammonium salt of glyphosate having a viscosity less than a similarly formulated composition of the IPA salt of glyphosate, and having a specific gravity greater than a similarly formulated composition of the IPA salt of glyphosate;
(2) adjusting said solution if necessary with water and/or other ingredients to form an adjusted solution having a glyphosate acid equivalent concentration between about 30 percent by weight and a maximum percentage by weight dictated by the solubility of said salt;
(3) substantially filling a bulk container having a capacity of about 15,000 to about 100,000 liters or more with said adjusted solution;
(4) securing said bulk container in or on a road or rail vehicle or water-borne vessel in a loading location; and
(5) causing said vehicle or vessel after loading to move from the loading location to an unloading location.

17. The method of claim 16 wherein said adjusted solution is further adjusted with a surfactant component in solution or stable dispersion in said water, comprising one or more surfactants in a total amount of about 20 to about 200 grams per liter of the composition and wherein said surfactant component is selected such that the composition exhibits no phase separation at temperatures of about 50° C. or lower.

18. The method of claim 17 wherein said surfactant component is selected such that the composition exhibits substantially no crystallization of said glyphosate or salt thereof when stored at a temperature not lower than about 0° C. for a period of up to about 7 days.

* * * * *